(12) United States Patent
Nishiyama et al.

(10) Patent No.: US 11,756,408 B2
(45) Date of Patent: Sep. 12, 2023

(54) COMMUNICATION TERMINAL AND RESCUE SYSTEM

(71) Applicant: Toyota Jidosha Kabushiki Kaisha, Toyota (JP)

(72) Inventors: Masahiro Nishiyama, Toyota (JP); Kenji Tsukagishi, Toyota (JP); Takahisa Kaneko, Toyota (JP); Erina Kigoshi, Tokyo (JP); Aiko Miyamoto, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 23 days.

(21) Appl. No.: 17/244,052

(22) Filed: Apr. 29, 2021

(65) Prior Publication Data

US 2022/0020264 A1    Jan. 20, 2022

(30) Foreign Application Priority Data

Jul. 15, 2020  (JP) .................................. 2020-121217

(51) Int. Cl.
| | |
|---|---|
| G08B 25/10 | (2006.01) |
| G08B 25/01 | (2006.01) |
| G08G 1/00 | (2006.01) |
| G08G 1/0967 | (2006.01) |
| G08B 21/02 | (2006.01) |
| G16H 40/20 | (2018.01) |

(52) U.S. Cl.
CPC .......... *G08B 25/016* (2013.01); *G08B 21/02* (2013.01); *G08B 25/10* (2013.01); *G08G 1/096716* (2013.01); *G08G 1/205* (2013.01); *G16H 40/20* (2018.01)

(58) Field of Classification Search
CPC ............................. G08B 25/016; G08B 25/10
See application file for complete search history.

(56) References Cited

U.S. PATENT DOCUMENTS

| | | | |
|---|---|---|---|
| 10,887,561 B2* | 1/2021 | Oami ..................... | G08B 25/04 |
| 2008/0242261 A1* | 10/2008 | Shimanuki ........... | G08B 25/016 |
| | | | 455/404.2 |
| 2009/0284348 A1* | 11/2009 | Pfeffer ................. | G08B 25/006 |
| | | | 340/7.3 |
| 2011/0117878 A1* | 5/2011 | Barash ................ | G08B 25/016 |
| | | | 340/539.12 |
| 2016/0298977 A1* | 10/2016 | Newlin ............. | G01C 21/3679 |
| 2019/0174289 A1* | 6/2019 | Martin .................... | H04W 4/90 |

FOREIGN PATENT DOCUMENTS

| | | |
|---|---|---|
| JP | H11353576 A | 12/1999 |
| JP | 2001-339536 A | 12/2001 |
| JP | 2017-034361 A | 2/2017 |

* cited by examiner

*Primary Examiner* — Qutbuddin Ghulamali
(74) *Attorney, Agent, or Firm* — Dinsmore & Shohl LLP

(57) ABSTRACT

A communication terminal includes a touch panel provided with a display device and an input device. The touch panel displays a request to rescue a rescued person and displays a plurality of modes of transportation to go to the rescued person and a travel time for each of the modes of transportation. The touch panel is provided with a reply button for selecting one of the modes of transportation and inputting a reply of going to the rescued person. The touch panel can also display a map showing a location of the rescued person or information on a symptom of the rescued person.

4 Claims, 9 Drawing Sheets

FIG. 5

| CALL RECORD | | | | | | |
|---|---|---|---|---|---|---|
| DATE AND TIME | LOCATION | COORDINATES | AGE | GENDER | SYMPTOMS | DETAILS |
| 2020/5/18 15:20.35 | INTERSECTION OF S STREET AND T STREET (1-1, E-CITY) | (x1, y1) | ABOUT ELEMENTARY SCHOOL AGE | FEMALE | INJURY | TRAFFIC ACCIDENT INJURED HEAVY BLEEDING UNCONSCIOUS |

FIG. 6

REGISTERED USER LIST

| ID | NAME | QUALIFI-CATION | SPECIALTY | FIELD OF SUPPORT | AREAS OF SUPPORT | AVAILABLE TIME | TRANSPORTATION USED | PAST RECORDS | CONTACT INFORMA-TION |
|---|---|---|---|---|---|---|---|---|---|
| 501 | AAAA | DOCTOR | OPHTHAL-MOLOGY | GENERAL | E-CITY, F-CITY | LINKED WITH THE SCHEDULE SYSTEM | WALK, BICYCLE, CAR | RESPONDED TWICE DID NOT RESPOND 0 TIMES | ... |
| 502 | BBBB | DOCTOR | INTERNAL MEDICINE | INTERNAL MEDICINE | E-CITY | WEEKDAYS 19-24 | WALK, BICYCLE | RESPONDED ONCE DID NOT RESPOND TWICE | ... |
| 503 | CCCC | NURSE | SURGERY | SURGERY | E-CITY, G-CITY | MONDAY 8-23 SUNDAY 8-23 | WALK, BICYCLE, CAR | RESPONDED ONCE DID NOT RESPOND 0 TIMES | ... |
| ... | ... | ... | ... | ... | ... | ... | ... | ... | ... |

FIG. 7

CANDIDATE LIST

| PRIORITY | NAME | QUALIFI-CATION | SPECIALTY | FIELD OF SUPPORT | ESTIMATED TRAVEL TIME | | PAST RECORDS | REQUEST |
|---|---|---|---|---|---|---|---|---|
| 1 | AAAA | DOCTOR | OPHTHAL-MOLOGY | GENERAL | WALK | 20 MINUTES | RESPONDED TWICE DID NOT RESPOND 0 TIMES | REQUEST |
| | | | | | BICYCLE | 8 MINUTES * | | |
| | | | | | CAR | 4 MINUTES *** | | |
| 2 | CCCC | NURSE | SURGERY | SURGERY | WALK | 13 MINUTES | RESPONDED ONCE DID NOT RESPOND 0 TIMES | REQUEST |
| | | | | | CAR | 6 MINUTES ** | | |

FIG. 8

CAN YOU GO TO RESCUE?
(REPLY REQUIRED)

[STATUS]

LOCATION: INTERSECTION OF S STREET AND T STREET (NEAR 1-1, E-CITY)
TIME OF CALL: 2 MINUTES AGO
RESCUED PERSON: 1 PERSON
CONDITION: TRAFFIC ACCIDENT, INJURED, HEAVY BLEEDING, UNCONSCIOUS
EMERGENCY MEDICAL STAFF: 15 MINUTES TO ARRIVE

| TRANSPOR-TATION | TRAVEL TIME | REPLY | |
|---|---|---|---|
| CAR | 4 MINUTES | YES | NO |
| BICYCLE | 6 MINUTES | YES | NO |

COMMUNICATION TERMINAL AND RESCUE SYSTEM

CROSS-REFERENCE TO RELATED APPLICATION

This application claims priority to Japanese Patent Application No. 2020-121217 filed on Jul. 15, 2020, incorporated herein by reference in its entirety.

BACKGROUND

1. Technical Field

The present disclosure relates to a communication terminal and a rescue system regarding rescue of a rescued person.

2. Description of Related Art

There is a known system for making a request for rescue to nearby people until an emergency medical staff arrives at a rescued person in need of rescue due to a sudden illness or an accident.

Japanese Unexamined Patent Application Publication No. 2017-34361 (JP 2017-34361 A) describes a device for quickly dispatching healthcare workers and the like to the current location of the rescued person. Specifically, when the rescued person transmits a request for rescue with the mobile terminal, a server that has accepted the transmission selects a registered user near the rescued person as a rescuer and transmits the request for rescue. On the mobile terminal of the registered user, a message requesting rescue, map information, and the current location of the rescued person are displayed. The registered user transmits a reply indicating whether he/she intends to go to the rescue with a button of the mobile terminal.

Japanese Unexamined Patent Application Publication No. 2001-339536 (JP 2001-339536 A) describes a method for calling fire engines, ambulances, emergency medical institutions, or the like. Here, when the rescued person makes an emergency call from the mobile terminal, the mobile terminal is first connected to a location information center. The location information center detects the location of the rescued person based on the global positioning system (GPS) information of the mobile terminal, and then selects the nearest emergency contact by referring to the map information data. Then, the location information center makes a call to the emergency contact, transfers the location information when receiving a reply, and connects the rescued person with the emergency contact. When the emergency contact is an emergency medical institution and there is no response, nearby emergency medical institutions are called in sequence.

SUMMARY

When the rescuer goes to the rescued person, the travel time varies depending on the mode of transportation such as walk and vehicles. In the above Japanese Unexamined Patent Application Publication No. 2017-34361 (JP 2017-34361 A), the travel time according to the mode of transportation is not taken into consideration, so it is not always possible to select an appropriate rescuer.

An object of the present disclosure is to improve the selection of a rescuer who goes to the rescued person and to accelerate the arrival of the rescuer.

A communication terminal according to a first aspect of the present disclosure includes: a display device that displays a request to rescue a rescued person and displays a plurality of modes of transportation to go to the rescued person and a travel time for each of the modes of transportation; and an input device for selecting one of the modes of transportation and inputting a reply of going to the rescued person.

In the first aspect, the display device may further display a map showing a location of the rescued person.

In the first aspect, the display device may further display information on a symptom of the rescued person.

In the first aspect, the display device may perform display that emphasizes a mode of transportation that is able to arrive earliest among the modes of transportation.

A rescue system according to a second aspect of the present disclosure causes a communication terminal to perform: display of a request to rescue a rescued person; display of a plurality of modes of transportation to go to the rescued person and a travel time for each of the modes of transportation; and display of an input unit for selecting one of the modes of transportation and inputting a reply of going to the rescued person.

According to each aspect of the present disclosure, since the travel time of the rescuer according to the mode of transportation is taken into consideration, it can be expected that the rescuer is selected appropriately and the arrival time to arrive at the rescued person is shortened.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 4 is a flowchart showing a processing flow in the rescue server and the like;

FIG. 5 is a diagram showing an example of emergency call records;

FIG. 6 is a diagram showing an example of a registered user list;

FIG. 7 is a diagram showing an example of a candidate list;

FIG. 8 is a diagram showing an example of a rescue request screen displayed on a communication terminal of a candidate.

DETAILED DESCRIPTION OF EMBODIMENTS

Hereinafter, embodiments will be described with reference to the drawings. In the description, specific modes are shown for ease of understanding, but these are examples of the embodiments, and various other embodiments are conceivable.

(1) Configuration of Rescue System

Figure 1:
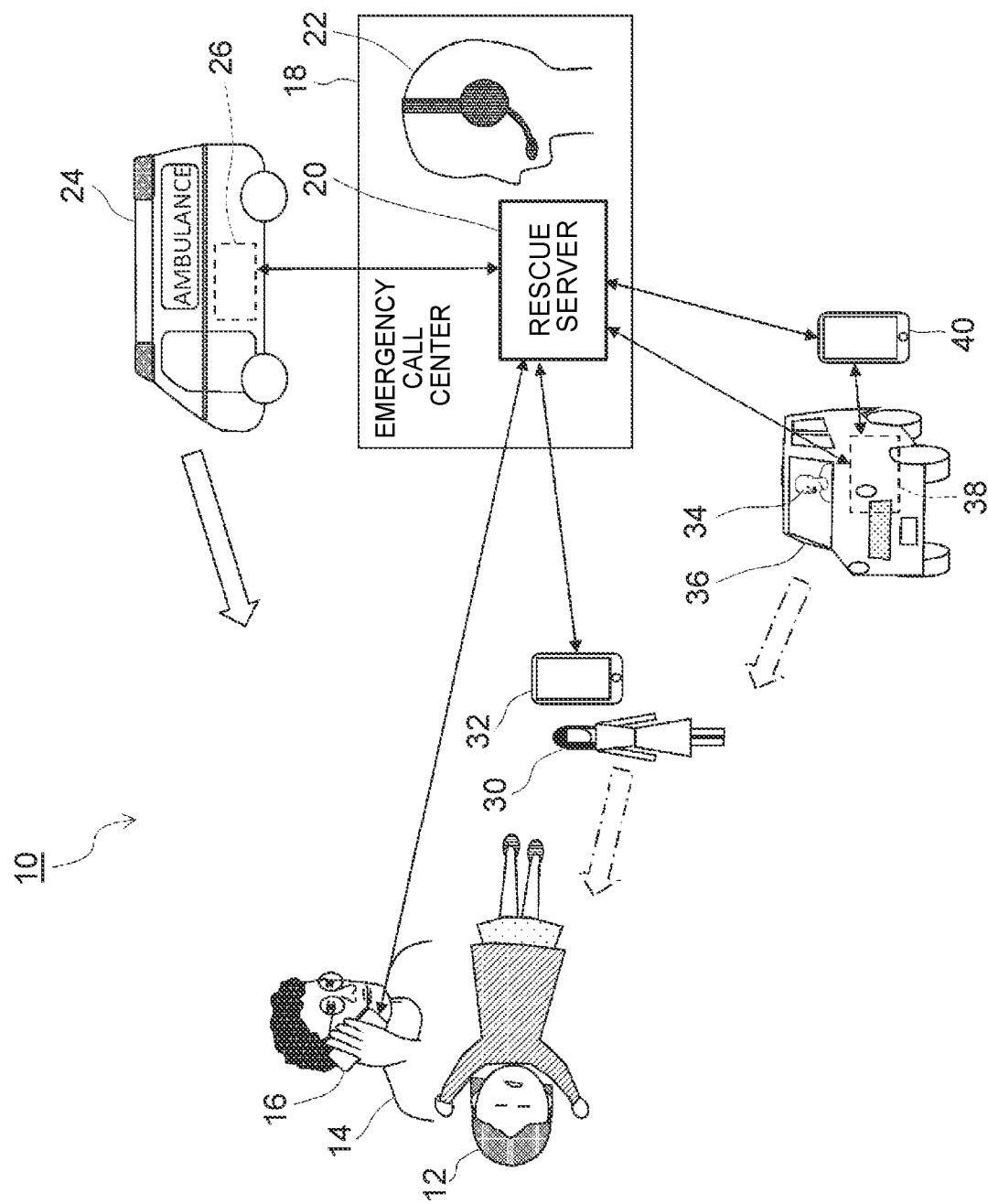
FIG. 1 is a schematic diagram showing an overall configuration of a rescue system.

FIG. 1 is a schematic diagram showing an overall configuration of a rescue system 10 according to an embodiment. The rescue system 10 is a system for promptly dispatching a rescuer that performs rescue to a rescued person 12 who needs urgent rescue due to injury, illness, or the like. In FIG. 1, it is assumed that the rescued person 12 is an elementary school girl who was injured in a traffic accident.

Beside the rescued person 12, a caller 14 is holding a smartphone 16, which is his own communication terminal, and making an emergency call. The call is connected to a rescue server 20 of an emergency call center 18 established publicly or privately.

The rescue server 20 is installed in the emergency call center 18. The rescue server 20 is a core device of the rescue system 10, receives emergency calls, and performs various processes described later. An operator 22 working at the emergency call center 18 inputs data of information obtained from the call into the rescue server 20 for the emergency calls. Further, the operator 22 instructs an emergency medical staff that boards an ambulance 24 to go to the rescued person 12. An in-vehicle communication device 26, which is a communication terminal, is installed in the ambulance 24. The in-vehicle communication device 26 can communicate with the rescue server 20, and the emergency medical staff can make a call with the operator 22 and the like, and view data related to the rescued person 12, for example. The communication terminal refers to a device capable of wired or wireless communication. The communication terminal may be a mobile terminal, or may be an immobile terminal. In addition to the in-vehicle communication device 26, the communication terminal includes, for example, a smartphone, a mobile phone, a laptop computer, a tablet computer, and the like.

The rescue system 10 aims to search for a healthcare worker or the like near the rescued person 12 and dispatch the healthcare worker to the rescued person 12 earlier than the emergency medical staff when it takes a relatively long time for the emergency medical staff to arrive at the rescued person 12. In the example of FIG. 1, a healthcare worker 30 who is a nurse is walking in a place relatively close to the rescued person 12. The healthcare worker 30 has a smartphone 32 that is a communication terminal. In the example of FIG. 1, another healthcare worker 34 is riding in a vehicle 36, which is a four-wheeled vehicle, and is driving in a place slightly far from the rescued person 12. The vehicle 36 is equipped with an in-vehicle communication device 38 that is a communication terminal. In addition, the healthcare worker 34 has a smartphone 40 that is a communication terminal. The in-vehicle communication device 38 and the smartphone 40 are set to be able to communicate with each other, and the same indication is displayed.

In the emergency call center 18, the rescue server 20 acquires the location information of the healthcare workers 30, 34 that are registered users. Further, the rescue server 20 calculates the times at which the healthcare workers 30, 34 arrive at the rescued person 12 in consideration of modes of transportation. When it is expected that the healthcare workers 30, 34 can arrive earlier than the emergency medical staff, the rescue server 20 requests the healthcare workers 30, 34 to go to the rescued person 12. The healthcare workers 30, 34 reply to the request through the smartphones 32, 40 and the in-vehicle communication device 38. When receiving the request, the healthcare workers 30, 34 go to the rescued person 12.

The system configuration shown above can be changed in various ways. For example, it is possible to set a part of the rescue server 20 in a remote place connected by a communication network.

Figure 2:
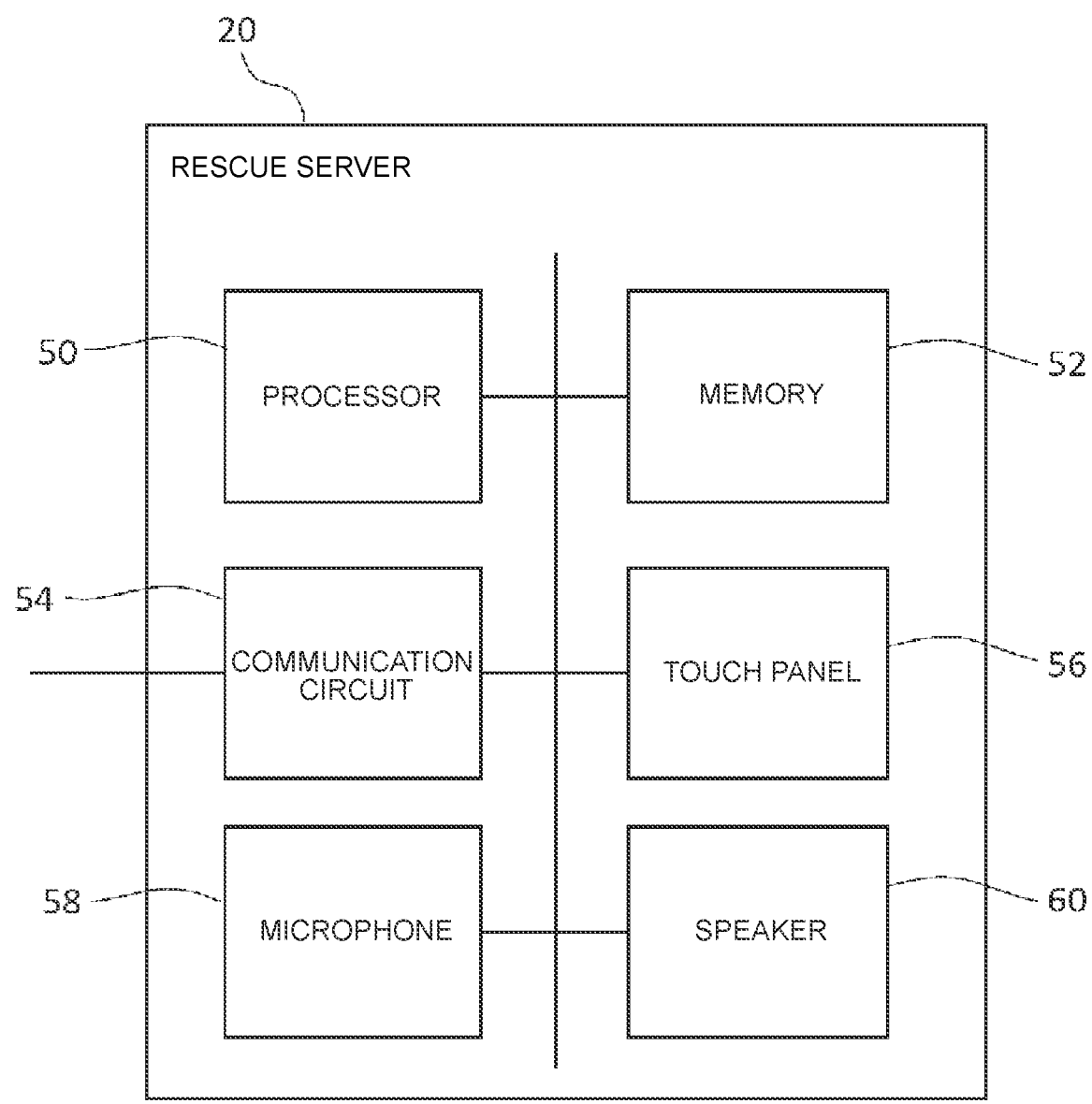
FIG. 2 is a block diagram showing a hardware configuration of a rescue server.

FIG. 2 is a simplified block diagram illustrating a hardware configuration of the rescue server 20. The rescue server 20 is provided with a processor 50, a memory 52, a communication circuit 54, a touch panel 56, a microphone 58, a speaker 60, and the like.

The processor 50 is a device that performs arithmetic processing, such as a central processing unit (CPU) and a graphics processing unit (GPU). A plurality of processors 50 may be provided in the rescue server 20, but only one processor 50 is symbolically shown in FIG. 2.

The memory 52 is a device that stores data, and is composed of a semiconductor memory, a hard disk, and the like. A plurality of memories 52 are often provided in the rescue server 20, but only one memory 52 is symbolically shown in FIG. 2.

The communication circuit 54 is a circuit for performing wired or wireless communication with the outside according to a predetermined protocol. The touch panel 56 is a device including a display that is a display device for displaying images and an input device for detecting an operation on the surface of the display. Of these, the display is an example of a candidate display unit, and also displays a list of candidates to go to the rescue. As the input device, for example, a keyboard, a mouse, or the like may be provided. The microphone 58 is a device that detects a voice of the operator 22 and converts the voice into electric signals. The speaker 60 is a device that converts electric signals into a voice.

In the rescue server 20, software such as an operating system (OS) and an application program is installed and stored in the memory 52. The software controls the operation of computer hardware including the processor 50, the memory 52, the communication circuit 54, and the touch panel 56. In addition, audio input/output through the microphone 58 and the speaker 60 is also performed under the control of the computer hardware and software. As a result, various functions described below with reference to FIG. 3 are implemented in the rescue server 20.

The rescue server 20 can be composed of single piece of computer hardware. Further, the rescue server 20 may be provided by connecting multiple pieces of computer hardware such that the pieces of computer hardware can communicate with each other.

The smartphones 16, 32, 40 and the in-vehicle communication devices 26, 38 shown in FIG. 1 also have the same hardware as that of the rescue server 20 shown in FIG. 2, and the operations thereof are controlled by the installed software.

Figure 3:
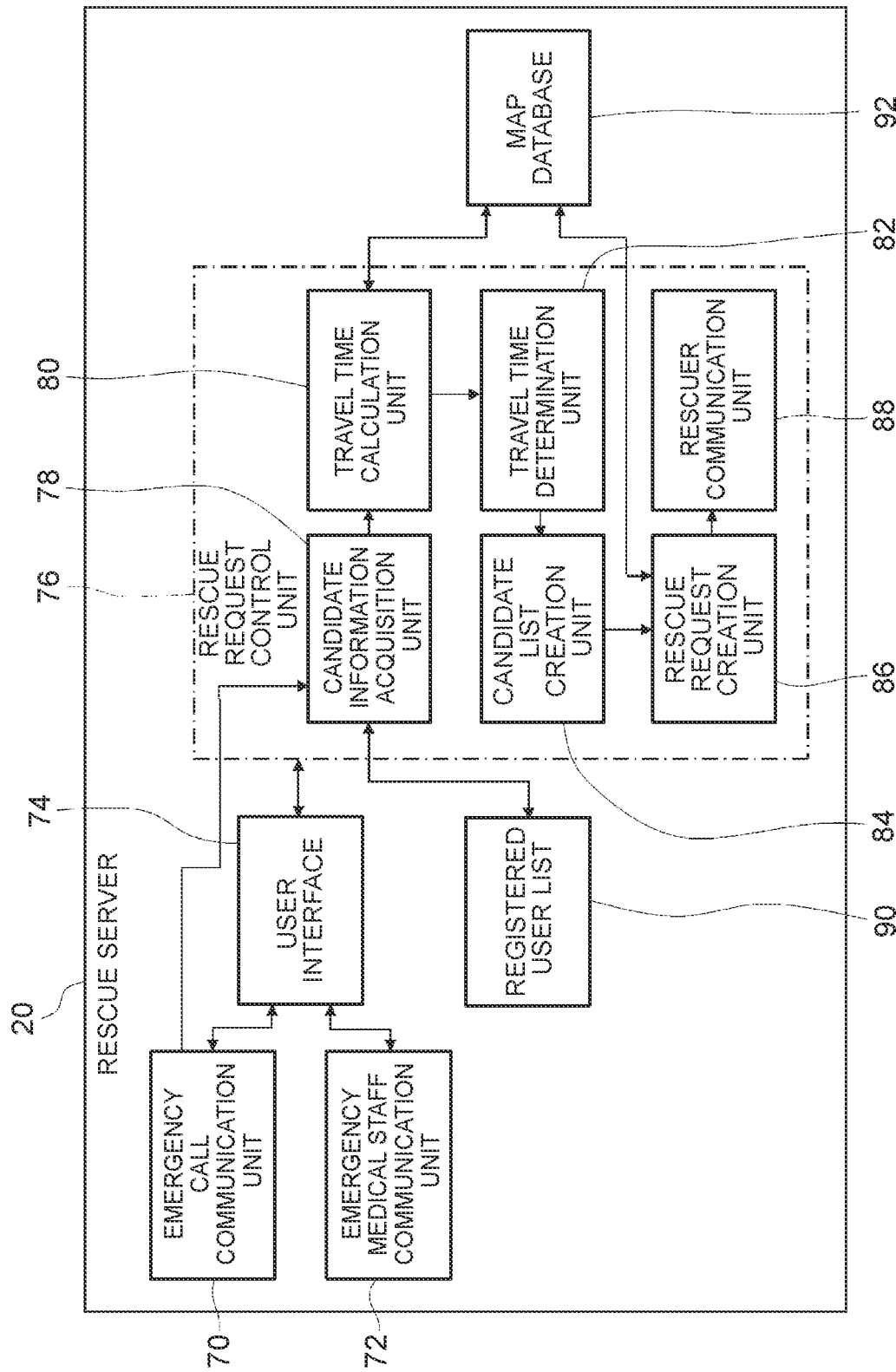
FIG. 3 is a block diagram showing a functional configuration of the rescue server.

FIG. 3 is a block diagram showing a functional configuration of the rescue server 20. In the rescue server 20, an emergency call communication unit 70, an emergency medical staff communication unit 72, a user interface 74, a rescue request control unit 76, a registered user list 90, and a map database 92 are provided.

The emergency call communication unit 70 is an example of a receiver, and performs communication including reception and response of an emergency call. Specifically, the emergency call communication unit 70 receives an emergency call from the smartphone 16 or the like through a call line, and the operator 22 responds to the call. Further, the emergency call communication unit 70 can also receive set emergency call data when, for example, the emergency call button set on the smartphone 16 or the like is pressed. With the emergency call, for example, the location information of the rescued person is transmitted to the emergency call center 18 together with information on the rescued person such as the number of rescued people, age, gender, and symptoms of each rescued person. The location information is transmitted from the caller 14 through the call, or is automatically transmitted from the smartphone 16 or the like. As the location information automatically transmitted, for example, information acquired by the global navigation satellite system (GNSS) of the smartphone 16 or information estimated based on the radio wave condition of the radio base station is used. In addition, the location information of the installation location of the fixed telephone, which is associated with the telephone number, may be automatically transmitted. The automatically acquired location information is sent to the candidate information acquisition unit 78 in the rescue request control unit 76.

Under the instruction of the operator 22, the emergency medical staff communication unit 72 instructs the emergency medical staff to go to the rescue and also contacts the dispatched emergency medical staff. In addition, as will be described later, the emergency medical staff communication unit 72 also performs communication for the emergency medical staff and the rescuer to make calls or the like.

The user interface 74 is constructed using the touch panel 56 or the like, and is used by the operator 22 to operate the rescue server 20 or the like. The user interface 74 is an example of a candidate display unit, and also displays a list of candidates to go to the rescue.

The rescue request control unit 76 makes a request for rescue to the registered user. The rescue request control unit 76 includes a candidate information acquisition unit 78, a travel time calculation unit 80, a travel time determination unit 82, a candidate list creation unit 84, a rescue request creation unit 86, and a rescuer communication unit 88.

The candidate information acquisition unit 78 is an example of an acquisition unit. When there is an emergency call, the candidate information acquisition unit 78 first acquires the location information of the caller of the emergency call from the emergency call communication unit 70. Next, the candidate information acquisition unit 78 acquires information on the registered users that can be dispatched to the location of the location information from the registered user list 90. Then, based on the acquired information on the registered users, the candidate information acquisition unit 78 communicates with the communication terminals of the registered users, and acquires the location information of the communication terminals. It is also conceivable that the caller of the emergency call is in a different location from the rescued person 12. In this case, the caller of the emergency call informs the operator 22 of the location of the rescued person 12. Then, based on the location information input by the operator 22 to the user interface 74, the registered users that are the candidates for the rescuer are selected again.

The travel time calculation unit 80 is an example of an emergency medical staff arrival time estimation unit and a user arrival time estimation unit, and calculates the travel times required for the registered users that are the candidates to go to the rescued person 12 and the travel time required for the emergency medical staff to go to the rescued person 12. The travel times of the registered users are calculated for the plurality of modes of transportation listed in the registered user list 90.

The travel time determination unit 82 is an example of a determination unit, and compares the travel time of the emergency medical staff with the travel times of the registered users. Thus, registered users that can arrive at the rescued person 12 earlier than the emergency medical staff and the modes of transportation thereof can be obtained.

The candidate list creation unit 84 creates a list of candidates for the rescuer of the rescued person 12. The candidate list is created in consideration of the travel times from the registered users that can arrive at the rescued person 12 earlier than the emergency medical staff. The candidate list is created, taking into consideration schedule information, expertise, past rescue records, etc. registered in the candidate list.

There are two methods for making a request to the candidates on the candidate list created by the candidate list creation unit 84. One is a method in which the operator 22 selects the candidates by referring to the candidate list. The other is a method in which the rescue request control unit 76 automatically selects the candidates from the candidate list in accordance with the priorities.

The rescue request creation unit 86 creates data for making a request for rescue to the candidates. The data includes map information, information about the situation of the rescued person, information for reply, and so on.

The rescuer communication unit 88 is an example of a transmitter, and communicates with the communication terminals of the candidates. Specifically, the rescuer communication unit 88 transmits a request for the rescuer, receives a reply, and transmits a rescue instruction after the reply. In addition, the rescuer communication unit 88 also performs communication that acts as a bridge when the emergency medical staff and the rescuer make a call or the like.

The registered user list 90 is a list in which healthcare workers and the like having rescue skills are registered in the rescue system 10. Examples of the healthcare workers having rescue skills include those with national qualifications, such as doctors, nurses, midwives, and paramedics. The rescue system 10 can be operated as a system in which healthcare workers and the like participate with no charge, but can also be operated as a system in which the healthcare workers and the like participate for fee. The healthcare workers and the like express their intention to participate in advance and register necessary items, as well as install necessary application programs on their own communication terminals to prepare for rescue requests.

The map database 92 stores a map having an accuracy enough to set a travel route for each mode of transportation and calculate a travel time. The map in the map database 92 is also used for navigation when the rescuer is heading for the rescued person 12.

(2) Specific Example of Rescue System

Figure 4:
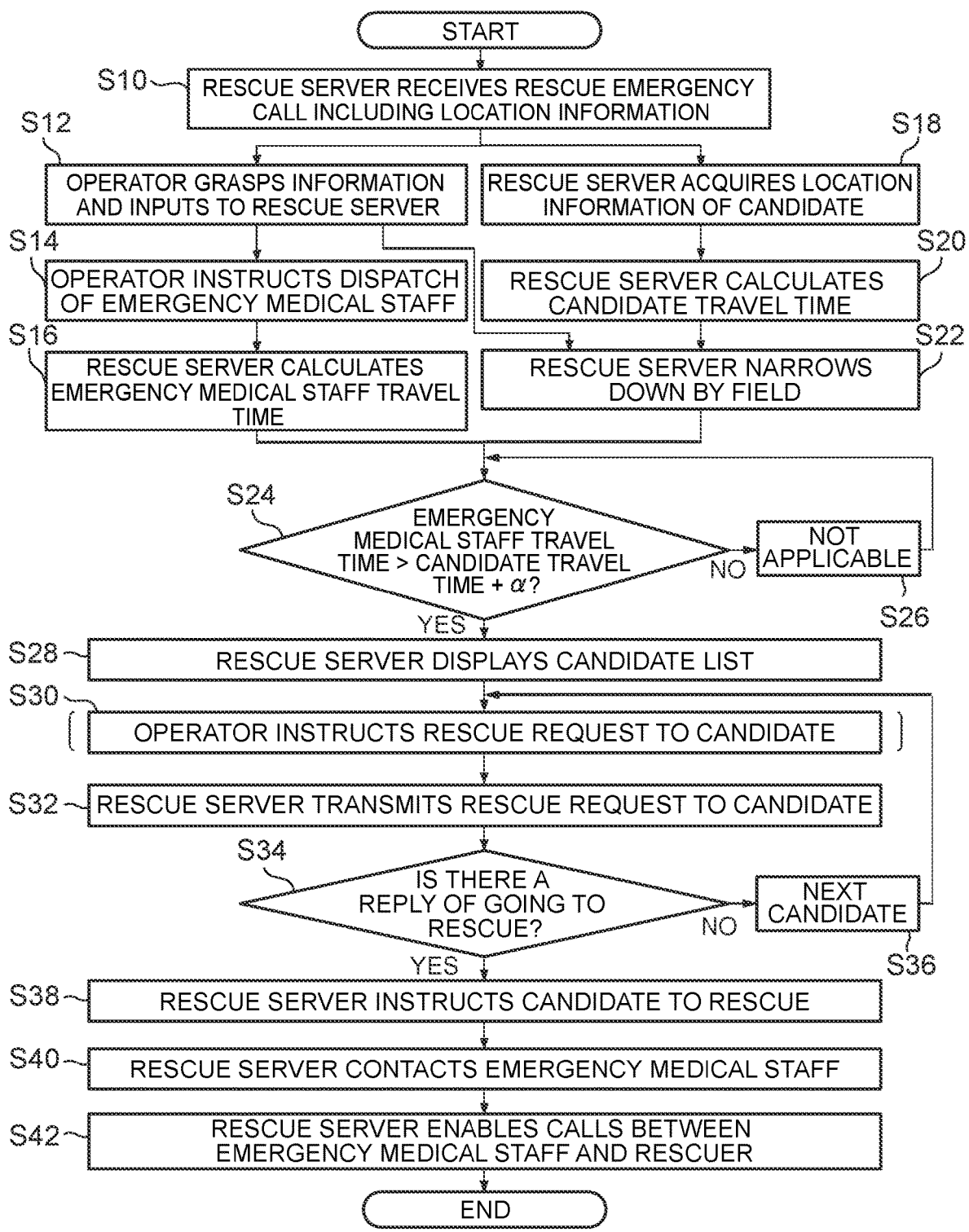
Figure 9:
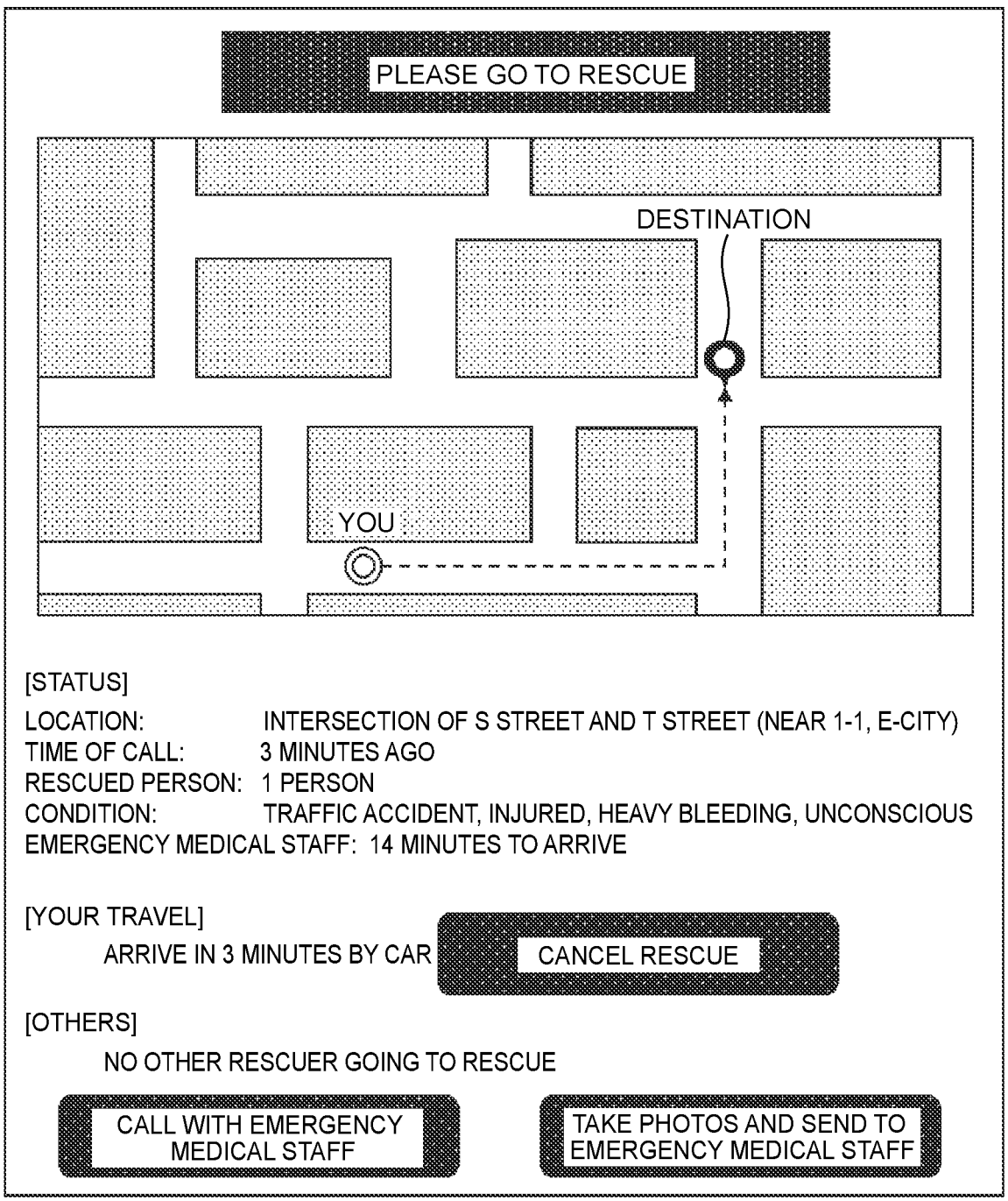
FIG. 9 is a diagram showing an example of a rescue instruction screen displayed on a communication terminal of a rescuer.

A specific example of the rescue system 10 will be described with reference to FIGS. 4 to 9. FIG. 4 is a flowchart showing an example of the operation of the rescue system 10. FIG. 5 is a diagram showing an example of call records. FIG. 6 is a diagram showing an example of the registered user list 90. FIG. 7 is a diagram showing an example of the candidate list. FIG. 8 is a diagram showing a display example of the terminal device to which a request for rescue has been made. FIG. 9 is a diagram showing a display example of the terminal device after the reply of going to the rescue is made.

In the example shown in FIG. 4, first, the emergency call communication unit 70 of the rescue server 20 receives the emergency call (S10). In the emergency call, the location information of the communication terminal used for the call is automatically acquired. In the emergency call, the caller tells the location information, conditions, etc. of the rescued person following the guidance of the operator 22 to make a request for rescue. The operator 22 grasps the information and inputs the information to the rescue server 20 through the user interface 74 (S12).

FIG. 5 shows an example of the call records input by the operator 22. In the present example, an emergency call was received at 15:20:35 on May 18, 2020. The location of the rescued person 12 is near the address of 1-1, E-city, and this address corresponds to the intersection of S street and T street. The coordinates (x1, y1) are information indicating the position where the rescued person 12 is located, and values that can be matched with the map of the map database 92 are used. For example, latitude and mild are used as coordinates. The rescued person 12 is a female of about elementary school age. The symptom of the rescued person 12 is an injury. In addition, as detailed information, information on the type of rescue and the symptom such as a traffic accident, injury, heavy bleeding, and unconsciousness is recorded.

While recording the call record, the operator 22 gives a dispatch instruction to the emergency medical staff through the emergency medical staff communication unit 72 (S14). When the dispatch instruction is given, the rescue server 20 calculates the time at which the emergency medical staff arrives at the rescued person with the travel time calculation unit 80 of the rescue request control unit 76 (S16).

At the same time, in the rescue server 20, the automatically acquired location information of the communication terminals is input to the candidate information acquisition unit 78 of the rescue request control unit 76. The candidate information acquisition unit 78 acquires the location information of the registered users that can provide rescue at the location indicated by the location information (S18). The location information of the registered users is acquired by referring to the registered user list.

FIG. 6 shows an example of the registered user list. The list includes items such as identification (ID), name, qualification, specialty, field of support, areas of support, available time, a mode of transportation to use, past records, and contact information. The ID is a number that uniquely identifies each registered user, and the name is the name of the registered user. As for the qualification, official qualifications as healthcare workers and the like are registered. The specialty indicates a field in which each registered user is professionally engaged as the healthcare worker and the like. The field of support indicates the field that each registered user has stated to be able to deal with. The areas of support indicate areas that each registered user has stated to be able to go to the rescue of the rescued person. The available time indicates the time range for which each registered user consents to perform the rescue operation. In the modes of transportation to use, modes of transportation that the registered user may use when going to the rescue are registered. The past records indicate the number of times the registered user responded to the rescue request and the number of times the registered user declined the rescue request and did not respond in the rescue system 10. In the contact Information, information for accessing the communication terminals of the registered users is registered.

In the example of FIG. 6, AAAA of ID501 is a doctor and routinely specializes in ophthalmology. However, AAAA has stated to be able to handle all the fields from surgery to internal medicine in the case of rescue, for example. The areas of support are E-city and F-city. As for the available time, it is registered that the schedule system should be referred to. Here, it is assumed that AAAA has registered his/her schedule in a cloud schedule system. This means that AAAA is requesting the rescue system 10 to grasp the available time with reference to that schedule.

The modes of transportation that may be used include a walk, a bicycle, and a car (four-wheeled vehicle). It is also recorded that AAAA responded to the rescue request twice and declined the rescue request 0 times.

Similarly, BBBB, CCCC and others are also registered. In the case of BBBB, who is a doctor, it is registered that his/her field of support is limited to internal medicine and he/she does not deal with traffic accidents but deal with sudden illnesses. The areas of support of BBBB is E-city, and the available time is from 19:00 to 24:00 on weekdays. CCCC, who is a nurse, covers E-city and G-city, with available time from 8:00 to 23:00 on Mondays and from 8:00 to 23:00 on Sundays.

The description will be continued with reference to the flowchart of FIG. 4. In step S18, the rescue server 20 first automatically acquires the coordinates (x1, y1) that are the location information. The coordinates indicate E-city, and the rescue server 20 communicates with the communication terminals of the registered users covering E-city, and acquires the current location information. The registered users covering E-city include AAAA, BBBB, and CCCC.

Then, the travel time calculation unit 80 calculates the travel time required for the registered user to arrive at the rescued person (S20). The travel time is calculated for all the modes of transportation registered in the registered user list.

Further, when the details input by the operator 22 to the rescue server 20 are acquired, the registered users having the expertise etc. required for the rescue are narrowed down (S22). In the example shown in FIG. 5, the symptom of the rescued person 12 is an injury, which is in the surgical field. For this reason, BBBB with his/her fields of support not including the surgical field is excluded, and AAAA and CCCC that cover the surgical field remain as the candidates. AAAA and CCCC are also left as the candidates because their available time match the time of the call.

Subsequently, the travel time determination unit 82 compares the travel time of the emergency medical staff with the travel times of the candidates (S24). As a result, the registered users that arrive later than the emergency medical staff are excluded from the candidates. In the example shown in FIG. 4, a registered user arriving at approximately the same time as the emergency medical staff is excluded, setting a condition that the user arrives earlier than the emergency medical staff by time a or more. As the time a, for example, one minute, three minutes, five minutes, or the like is selected. The candidate list creation unit 84 lists registered users satisfying the conditions of step S24 on the candidate list (S28).

FIG. 7 shows an example of the candidate list. The candidate list includes columns of priority, qualification, specialty, field of support, travel time, past records, and request. The priority indicates the priority for making a rescue request. In the example of FIG. 7, the priority is determined based on the travel time of the fastest mode of transportation. The columns for name, qualification, specialty, field of support, and past records are the same as those of the registered user list. For the travel time, the travel time calculated by the travel time calculation unit 80 is posted for each mode of transportation. In addition, the column for request is provided with "request" buttons that are examples of the acceptance unit. When the operator 22 operates the "request" button, the rescue request control unit 76 accepts the rescue request to the registered user.

In the example of FIG. 7, the first priority is AAAA. AAAA is located 20-minute walk, eight-minute bicycle ride, and four-minute drive away. Of these, walk is excluded because AAAA will arrive later than the emergency medical staff, but bicycle and car enable arrival earlier than the emergency medical staff, so remain as the candidates. In particular, the arrival in four minutes by car highlighted by the symbol "***" indicates that it is the fastest of all the registered users. In addition, the arrival in eight minutes by bicycle highlighted by the symbol "*" indicates that it is the third fastest of all the registered users.

CCCC with the second highest priority is located 13-minute walk and six-minute drive away. Of these, the arrival in six minutes by car highlighted by the symbol "**" indicates that it is the second fastest of all the registered users.

In the example of FIG. 7, AAAA can realize the fastest (earliest) travel and the third fastest travel, and CCCC can realize the second fastest travel. For this reason, it is conceivable to ask AAAA to go by car that is the fastest, and if declined, ask CCCC to go by car that is the second fastest. On the other hand, considering the time required to ask CCCC after being declined by AAAA, it is possible to ask AAAA about the possibility of traveling both by car and bicycle.

As shown in the flowchart of FIG. 4, the candidate list is displayed on the touch panel 56, which is the user interface 74 of the rescue server 20. This makes it possible for the operator 22 to grasp the information of the rescuer candidate. The operator 22 can make a rescue request by selecting from the candidates and pressing the "request" button (S30). Alternatively, the rescue server 20 may automatically make a rescue request in accordance with the priority. When a rescue request is made, the rescue request creation unit 86 creates data for making the rescue request. Then, the rescue request is made by the rescuer communication unit 88 (S32).

FIG. 8 shows an example of the rescue request screen displayed on the communication terminal of the registered user who is a candidate. The indication "Can you go to rescue? (reply required)" is displayed in large size, indicating that the registered user is requested to go to the rescue and a reply thereto is required. Together with the screen display, it is also possible to output audio to call the attention of the registered users.

A map is also displayed on the screen. On the map, the location of the registered user is shown as the location of "You", the location of the rescued person is shown as the location of "Destination", and the travel route is indicated by the arrow.

In addition, the item "Status" is provided, and it is stated that the location is the intersection of S street and T street. S street and T street may be indicated on the map, but they are omitted in the example of FIG. 8. In addition, it is indicated that the time of the call was two minutes ago and there is one rescued person. The condition field shows information indicating a traffic accident, injured, heavy bleeding, unconscious, etc. and the emergency medical staff field shows that it takes 15 minutes to arrive.

The screen is also provided with a table containing modes of transportation, travel time and reply columns. In the example of FIG. 8, the buttons to reply whether to go by car or not to go by car are displayed with an indication of the travel time by car of four minutes. When the button of going by car is pressed, it is regarded that the intention to go by car has been expressed, and contact to the rescue server 20 is made and the reply is completed. In addition, when the button of not going by car is pressed, it is regarded that there is no intention to go to the rescue, and a contact to the rescue server 20 is made and the reply is completed. However, the rescue server 20 may be set such that when the button of not going by car is pressed, the rescue server 20 regards it that the registered user is withholding the reply whether to go or not to go by bicycle and continues to wait for the reply. Similarly, the screen is provided with a button to reply that the registered user will go by bicycle and a button to reply that the registered user will not go by bicycle, with the travel time by bicycle of eight minutes being indicated.

When there is a reply not to go to the rescue in step S34 of FIG. 4, a candidate with the next priority is selected (S36) and contacted. However, while waiting for a reply from the candidate, the emergency medical staff approaches the rescued person, so it is possible that the next candidate will not be selected. On the other hand, when there is a response to go to the rescue, the rescue server 20 sets the registered user as the rescuer and gives a rescue instruction (S38). In addition, the rescue server 20 notifies the emergency medical staff of information that the rescuer is going to the rescue (S40).

FIG. 9 shows an example of a screen that can be switched from the screen of FIG. 8. Here, the instruction "Please go to the rescue" is indicated. The map is displayed in the same manner as in FIG. 8 and shows the latest location of "You". The status field is updated to the latest status as necessary. In the example of FIG. 9, the columns of the time of call and the emergency medical staff are updated. For example, when the emergency medical staff travels faster than expected and can arrive at the rescued person earlier than the rescuer, the rescuer can also cancel traveling.

The screen also has an item of "Your travel". Here, it is assumed that the rescuer replies that he/she will go by car. Thus, it is displayed that he/she will arrive in three minutes by car. In addition, a "Cancel rescue" button is provided next to it. This button is pressed when there is a sudden situation where the rescuer cannot go to the rescued person or when the travel may take longer than expected. When the button is pressed, the fact that the user cannot go is transmitted to the rescue server 20, and the emergency medical staff is also notified of it.

In addition, the item of others is provided on the screen, and it is stated that there is no other rescuer heading for. For example, when there are a number of rescued people, or when it is desired to ensure that the rescuer is dispatched to the rescued person, a plurality of registered users may be set as the rescuers. When the plurality of rescuers go to the rescued person, the location information of the other rescuers may be displayed on the map. Alternatively, it is possible to respect the privacy of other rescuers and not to display the location information.

At the bottom of the screen, there is a "Call with emergency medical staff" button and a "Take photos and send to emergency medical staff" button. These are provided to provide rescue in cooperation with the emergency medical staff when arriving at the rescued person.

As shown in step S42 of FIG. 4, when the "Call with emergency medical staff" button is pressed, the rescue server 20 connects the communication so that the emergency medical staff and the rescuer can talk to each other. The operator 22 can also join the call.

When the "Take photos and send to emergency medical staff" button is pressed, the camera of the communication terminal is activated and the photographs taken are immediately sent to the emergency medical staff. The photographs can also be viewed by the operator 22.

In addition to the examples shown in FIGS. 8 and 9, various screen displays can be set. In the examples of FIGS. 8 and 9, all the information is displayed on one screen, and scrolling and page breaks are not required. However, it is conceivable to display large characters or the like and require scrolling or page breaks. Alternatively, it is conceivable that important information is provided on the top page and detailed information is provided on the next and subsequent pages.

What is claimed is:

1. A communication terminal comprising:

a display device that displays a request to rescue a rescued person and displays a plurality of modes of transportation to go to the rescued person and a travel time for each of the modes of transportation, the display device performs display that emphasizes a mode of transportation that is able to arrive earliest among the plurality of modes of transportation; and an input device for selecting one of the plurality of modes of transportation and inputting a reply of going to the rescued person, the input device further includes a call button configured to call emergency medical staff.

2. The communication terminal according to claim 1, wherein the display device further displays a map showing a location of the rescued person.

3. The communication terminal according to claim 1, wherein the display device further displays information on a symptom of the rescued person.

4. A rescue system that causes a communication terminal to perform:

display of a request to rescue a rescued person;

display of a plurality of modes of transportation to go to the rescued person and a travel time for each of the plurality of modes of transportation;

emphasize a mode of transportation that is able to arrive earliest among the plurality of modes of transportation; and display of an input device or selecting one of the plurality of modes of transportation and inputting a reply of going to the rescued person, the input device further includes a call button configured to call emergency medical staff.

* * * * *